(12) United States Patent
Chin et al.

(10) Patent No.: US 8,435,267 B2
(45) Date of Patent: May 7, 2013

(54) SPINE FIXATION METHOD AND APPARATUS

(75) Inventors: Kingsley Richard Chin, Philadelphia, PA (US); Matthew Ibarra, Lakewood, CA (US)

(73) Assignee: Spinefrontier Inc, Beverly, MA (US)

(*) Notice: Subject to any disclaimer, the term of this patent is extended or adjusted under 35 U.S.C. 154(b) by 1518 days.

(21) Appl. No.: 11/738,126

(22) Filed: Apr. 20, 2007

(65) Prior Publication Data

US 2007/0250061 A1   Oct. 25, 2007

Related U.S. Application Data

(60) Provisional application No. 60/794,355, filed on Apr. 24, 2006.

(51) Int. Cl.
*A61B 17/70* (2006.01)
(52) U.S. Cl.
USPC ........................................................ 606/264
(58) Field of Classification Search .............. 606/264, 606/265, 266, 267, 270, 278, 279
See application file for complete search history.

(56) References Cited

U.S. PATENT DOCUMENTS

| | | |
|---|---|---|
| 5,645,599 A | 7/1997 | Samani |
| 5,728,097 A | 3/1998 | Mathews |
| 5,882,344 A | 3/1999 | Stouder |
| 5,938,663 A | 8/1999 | Petreto |
| 6,440,137 B1 * | 8/2002 | Horvath et al. ............... 606/302 |
| 6,482,207 B1 | 11/2002 | Errico |
| 6,685,705 B1 | 2/2004 | Taylor |
| 6,793,656 B1 | 9/2004 | Matthews |
| 6,802,844 B2 | 10/2004 | Ferree |
| 7,090,674 B2 | 8/2006 | Doubler et al. |
| 7,166,109 B2 | 1/2007 | Biedermann et al. |
| 7,303,563 B2 * | 12/2007 | Poyner et al. ............... 606/279 |
| 7,618,443 B2 * | 11/2009 | Abdou ........................ 606/278 |
| 7,722,651 B2 * | 5/2010 | Kwak et al. .................. 606/265 |
| 7,740,649 B2 * | 6/2010 | Mosca et al. ................ 606/289 |

(Continued)

FOREIGN PATENT DOCUMENTS

| | | |
|---|---|---|
| EP | 1418854 | 5/2003 |
| WO | WO2007070819 A2 | 6/2007 |

(Continued)

*Primary Examiner* — Anu Ramana
(74) *Attorney, Agent, or Firm* — AKC Patents LLC; Aliki K. Collins

(57) ABSTRACT

A spine fixation assembly connecting a first vertebra to a second vertebra includes first and second mounting assemblies and a first spinal stabilization component. The first mounting assembly is configured to be attached to a first location of the first vertebra and includes a first bone anchor housing and first and second spinal stabilization component housings extending from the first bone anchor housing. The second mounting assembly is configured to be attached to a first location of the second vertebra and includes a second bone anchor housing and third and fourth spinal stabilization component housings extending from the second housing. The first spinal stabilization component includes an elongated body having a first end and a second end and is configured to connect the first mounting assembly to the second mounting assembly. The first spinal stabilization component housing is adapted to receive and connect to the first end of the spinal stabilization component and the third spinal stabilization component housing is adapted to receive and connect to the second end of the spinal stabilization component.

41 Claims, 12 Drawing Sheets

U.S. PATENT DOCUMENTS

| | | |
|---|---|---|
| 2003/0040746 A1 | 2/2003 | Mitchell et al. |
| 2003/0216736 A1 | 11/2003 | Robinson et al. |
| 2004/0039384 A1 | 2/2004 | Boehm et al. |
| 2006/0247640 A1 | 11/2006 | Blackwell et al. |
| 2006/0293662 A1 | 12/2006 | Boyer et al. |
| 2007/0162001 A1 | 7/2007 | Chin et al. |
| 2007/0179500 A1 | 8/2007 | Chin et al. |
| 2007/0233082 A1 | 10/2007 | Chin et al. |
| 2008/0167655 A1 | 7/2008 | Wang |
| 2008/0183211 A1 | 7/2008 | Lamborne et al. |
| 2010/0087860 A1 | 4/2010 | Chin et al. |
| 2010/0087869 A1 | 4/2010 | Abdou |
| 2011/0022090 A1 | 1/2011 | Gordon et al. |
| 2011/0144692 A1 | 6/2011 | Saladin et al. |

FOREIGN PATENT DOCUMENTS

| | | |
|---|---|---|
| WO | WO2010016949 A1 | 2/2010 |
| WO | WO2010068829 A2 | 6/2010 |
| WO | WO2011031924 A2 | 3/2011 |

\* cited by examiner

SPINE FIXATION METHOD AND APPARATUS

CROSS REFERENCE TO RELATED CO-PENDING APPLICATIONS

This application claims the benefit of U.S. provisional application Ser. No. 60/794,355 filed Apr. 24, 2006 and entitled "IMPROVED SPINE FIXATION METHOD AND APPARATUS, the contents of which are expressly incorporated herein by reference.

FIELD OF THE INVENTION

The present invention relates to an improved spine fixation method and apparatus, and more particularly to a spine fixation method and apparatus that utilizes adjustable, multi-axial mounting assemblies for receiving segments of stabilization elements with various geometries.

BACKGROUND OF THE INVENTION

Several prior art spine fixation assemblies utilize rods and/or plates as connecting and stabilization elements between vertebral elements. The rods are secured to vertebral bones left and right the spinal midline via screws. The screws in some of the prior art assemblies are capable of pivoting around a fixed axis of the stabilization rods to achieve variable angular positions relative to the rods. This limited range of relative angular positioning is acceptable for many spinal pathologies. However, in some cases it is preferred to have screws that provide multi-axial positioning relative to the stabilization rods.

Single or multilevel segmental posterior fusions are most commonly achieved by contouring a rigid ¼ inch cylindrical rod and attaching it to adjacent pedicle screws on each side of the spine using various connecting assemblies. This longitudinal construction can be made more rigid by connecting the rods to each other to form an "H" configuration. The rod system requires contouring of each rod across several vertebras in many cases. The contouring of each rod depends on the configuration of the pedicle screws and varies from side to side in the same patient and among patients. This may add considerable time to an operation. Recent generations of pedicle screws and rod connectors seek to diminish this drawback by allowing variable axes of movements in the pedicle screw recess for the rod or in the rod connectors. However, in most cases this adds another level of complexity to the operation and often further increases the operative time. This increase in operative time and the complexity of the connectors put substantial stress on the surgeon and the supporting staff. Even in the hands of the best spine surgeon, the rod is often not perfectly contoured to align with the pedicle screws. Hence the surgeon has to use substantial force at multiple points along a rod to hold the rod to the screws or connectors while counteracting the adjacent soft tissues. This maneuver risks soft tissue damage and also puts the dura and the neural contents at risk for dural tears or spinal cord or nerve damage if a holding instrument slips.

Accordingly, there is a need for an improved spinal fixation device and method that does not require rod contouring and allows multi-axial screw anchoring.

SUMMARY OF THE INVENTION

In general, in one aspect, the invention features a spine fixation assembly for connecting a first vertebra to a second vertebra including first and second mounting assemblies and a first spinal stabilization component. The first mounting assembly is configured to be attached to a first location of the first vertebra and includes a first bone anchor housing and first and second spinal stabilization component housings extending from the first bone anchor housing. The second mounting assembly is configured to be attached to a first location of the second vertebra and includes a second bone anchor housing and third and fourth spinal stabilization component housings extending from the second housing. The first spinal stabilization component includes an elongated body having a first end and a second end and is configured to connect the first mounting assembly to the second mounting assembly. The first spinal stabilization component housing is adapted to receive and connect to the first end of the spinal stabilization component and the third spinal stabilization component housing is adapted to receive and connect to the second end of the spinal stabilization component.

Implementations of this aspect of the invention may include one or more of the following features. The spinal stabilization component housing comprises a mounting plate extending from the bone anchor housing and a mounting element configured to be removable attached to the mounting plate. The spinal stabilization component housing is rotatable around an axis passing through the center of the bone anchor housing. Any of the bone anchor housings comprise a multi-axial bone anchor housing. The spinal stabilization component may be rods, plates, cables or wires. The geometric configuration of the first and second ends of the elongated body may be a sphere, cylinder, hemisphere, flat plate, cup, hammer, sphere with flat opposite surfaces, circular plate, semicircular plate, polyhedron, ring-shaped and cannulated shape. Any of the mounting assemblies is attached to the vertebral location via a bone anchor configured to be received within the bone anchor housing. The bone anchors may be screws, hooks, pins or poly-axial screws. The mounting elements comprise a seat having a bottom configured to be removable attached to the corresponding mounting plate and a top configured to receive any of the elongated body's ends and comprising a side portion having an opening through which the elongated body extends. First and second locking elements may secure the first end to the first mounting element and the second end to the third mounting element, respectively. A bone anchor locking element may secure a bone anchor head to any of the bone anchor housings. Any of the locking elements may be a screw, a screw with a flat bottom, a screw with a pointed bottom, a washer, a nut, a snap-in lock, or a breakaway screw. The spine fixation assembly may further include a second spinal stabilization component configured to connect the second mounting assembly to a third mounting assembly configured to be attached to a first location of a third vertebra. The spine fixation assembly may also include a third spinal stabilization component configured to connect the third mounting assembly to a fourth mounting assembly configured to be attached to a first location of a fourth vertebra. The first and second vertebras are adjacent vertebras or not adjacent vertebras. The locations of the vertebras where the mounting assemblies are attached include a pedicle, transverse processes, pars, lamina, vertebral body, sacrum, lateral mass, and occiput. The components of the spine fixation assembly may be made of stainless steel, titanium, gold, silver, nickel, alloys thereof, bone, polymer, composites, ceramics, plastic, absorbable material or combination thereof. The spinal stabilization components may have adjustable lengths.

In general in another aspect the invention features a mounting assembly configured to be attached to a vertebra including a bone anchor housing and first and second spinal stabilization component housings. The bone anchor housing is configured to receive a bone anchor for attaching the assembly to the vertebra. The first and second spinal stabilization component housings extend from the first bone anchor housing and are adapted to receive and connect to first and second spinal stabilization components, respectively, and thereby to connect the mounting assembly to other mounting assemblies configured to be attached to other vertebras. The bone anchor may be a poly-axial screw. Any of the spinal stabilization component housings may be rotatable around an axis passing through the center of the bone anchor housing. The mounting assembly may further include locking elements for securing the bone anchor to the bone anchor housing and the spinal stabilization components to the spinal stabilization housings, respectively.

In general, in another aspect, the invention features a method for connecting a first vertebra to a second vertebra including the following steps. First, providing a first mounting assembly comprising a first bone anchor housing and first and second spinal stabilization component housings extending from the first bone anchor housing and attaching the first mounting assembly to a first location of the first vertebra. Next, providing a second mounting assembly comprising a second bone anchor housing and third and fourth spinal stabilization component housings extending from the second housing and attaching the second mounting assembly to a first location of the second vertebra. Next, providing a first spinal stabilization component comprising an elongated body having a first end and a second end and being dimensioned to span the distance between the first mounting assembly and the second mounting assembly and then attaching the first end of the spinal stabilization component to the first spinal stabilization component housing and the second end of the spinal stabilization component to the third spinal stabilization component housing.

Among the advantages of this invention may be one or more of the following. The improved spinal fixation system allows segmented fixation of the spine in all three directions and multi-axial anchoring of the fixation elements. The use of multiple fixation locations enhances stability and reduces the operating time and risk for spinal injury during surgery. The multi-axial screw housings with the rod stabilization attachments are easy to use and can be easily adjusted before or after implantation.

The details of one or more embodiments of the invention are set forth in the accompanying drawings and description below. Other features, objects and advantages of the invention will be apparent from the following description of the preferred embodiments, the drawings and from the claims

BRIEF DESCRIPTION OF THE DRAWINGS

Referring to the figures, wherein like numerals represent like parts throughout the several views. Various embodiments of the present invention will now be discussed with reference to the appended drawings. It is appreciated that these drawings depict only typical embodiments of the invention and are therefore not to be considered limiting of its scope.

Referring to the figures, wherein like numerals represent like parts throughout the several views.

DETAILED DESCRIPTION OF THE INVENTION

Figure 1:
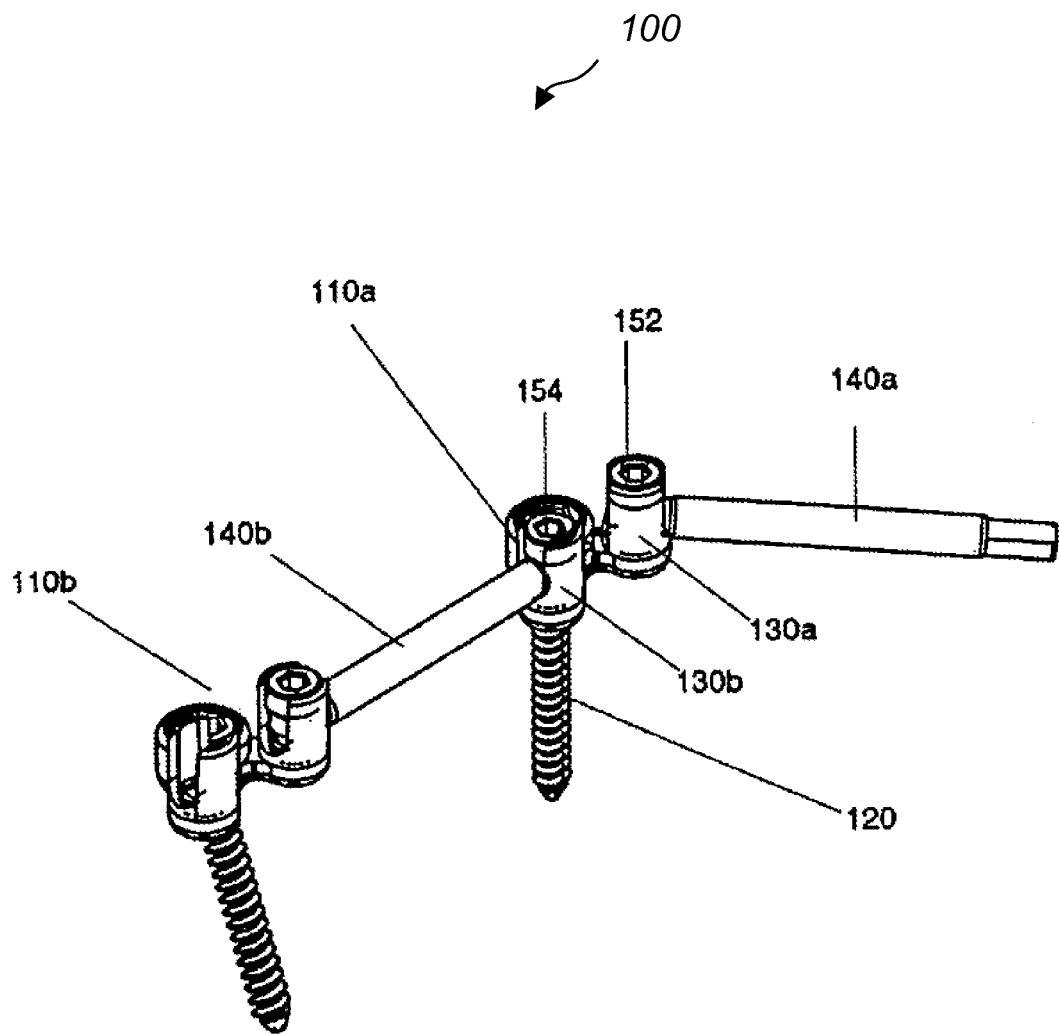
FIG. 1 is a perspective view of a first embodiment of an improved spine fixation apparatus that utilizes multi-axial screw assemblies according to this invention.
Figure 2:
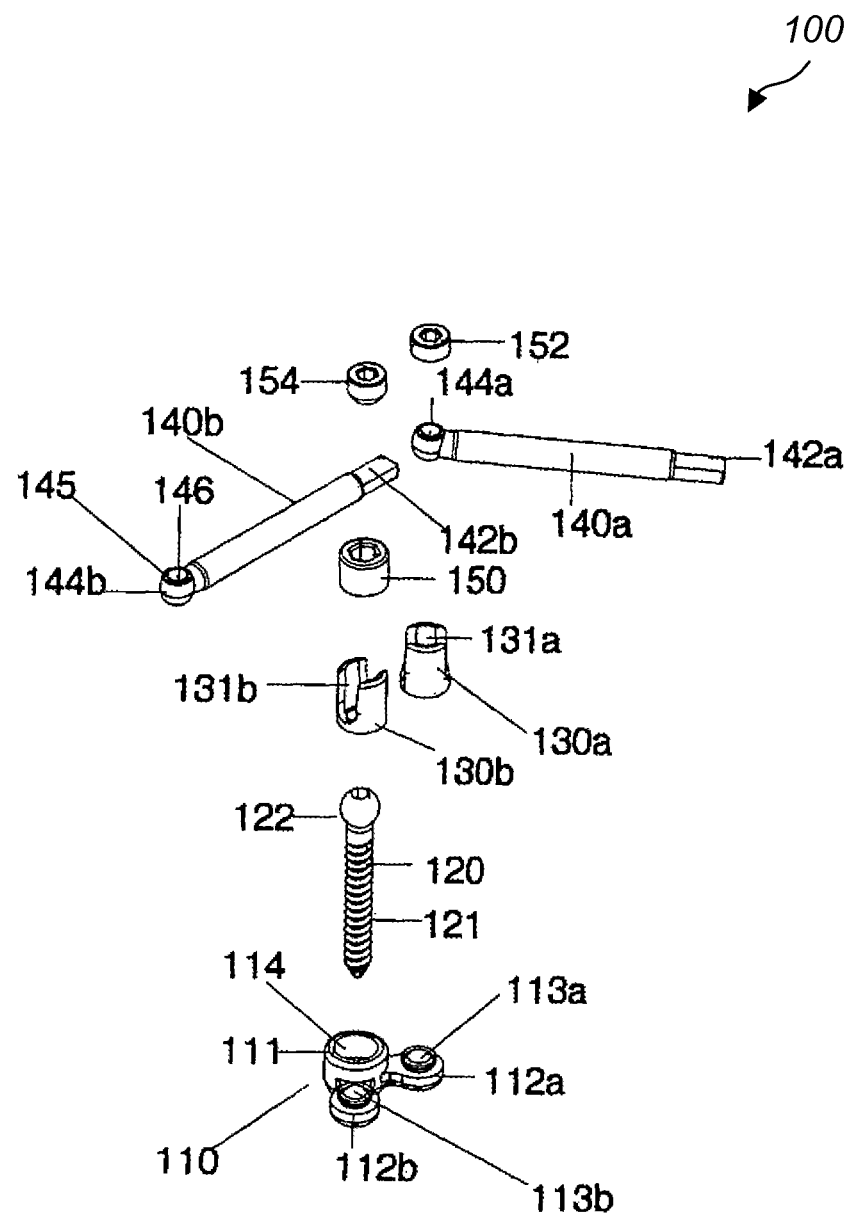
FIG. 2 is an exploded view of the spine fixation apparatus of FIG. 1.

The invention provides a spine fixation apparatus with a multi-axial screw assembly that utilizes a multi-axial screw housing and adjustable, mounting elements for receiving stabilization elements with various geometries Referring to FIG. 1, a spine fixation assembly 100 includes mounting assemblies 110*a*, 110*b* and stabilization rods 140*a*, 140*b*. Stabilization rod 140*b* is placed and secured in the mounting assemblies 110*a*, 110*b* and thereby connects them. Referring to FIG. 2, the mounting assembly 110 includes a multiaxial screw housing 111, two mounting plates 112*a*, 112*b* extending from the housing 111 and two mounting elements 130*a*, 130*b*. The screw housing 111 includes a through opening 114 for receiving a bone screw 120. Opening 114 extends from the top surface of the screw housing 111 to the bottom surface and has a diameter at the top larger than the diameter at the bottom. The bone screw 120 has a body 121 with outer threads and a spherical head 122. The body 121 is inserted through the opening 114 and is threaded into a vertebral bone (not shown). The spherical head 122 sits in the opening 114 of the screw housing 111 and the bone screw 120 is oriented at an angle 125 relative to the housing 111. This orientation of the screw 120 relative to the screw housing 111 is secured by a setscrew 150. Set screw 150 has outer threads that cooperate with inner threads of the opening 114. In this embodiment mounting plates 112*a*, 112*b* are fixed relative to the screw housing 111 and relative to each other. They have receiving elements 113*a*, 113*b*, that are used to attach the mounting elements 130*a*, 130*b* to the mounting plates 112*a*, 112*b*, respectively. The mounting elements 130*a*, 130*b* have a cylindrical shape and slot openings 131*a*, 131*b*, respectively, shaped and dimensioned to accommodate the ends 144*a*, 142*b* of the stabilization rods 140*a*, 140*b*. Each stabilization rod 140*a*, 140*b* has an elongated cylindrical body, a spherical end 144*a*, 144*b* and a slotted flat end 142*a*, 142*b*, respectively. The spherical end 144*a* has a flat top 145*a* with a concave dimple 146*a*. The slotted end 142*b* of rod 140*b* is placed in the slot opening 131*b* of the mounting element 130*b* and the spherical end 144*a* of rod 140*a* is placed in the slot opening 131*a* of the mounting element 130*a*. The flat top 145a with the concave dimple 146a of end 144a faces the same side as the flat surface of end 142b. The slotted end 142b is secured in the opening of the mounting element 130b with a set screw 154 that has a flat bottom that sits directly onto the flat surface of the slotted end 142b. The spherical end 144a is secured in the opening of the mounting element 130a with a set screw 152 that has a pointed bottom that sits directly into the dimple 146a of the spherical end 144a. Set screws 152, 154 secure the angular position of the rods 140a, 140b relative to the mounting elements 130a, 130b and therefore relative to the screw housing 111.

Figure 3:
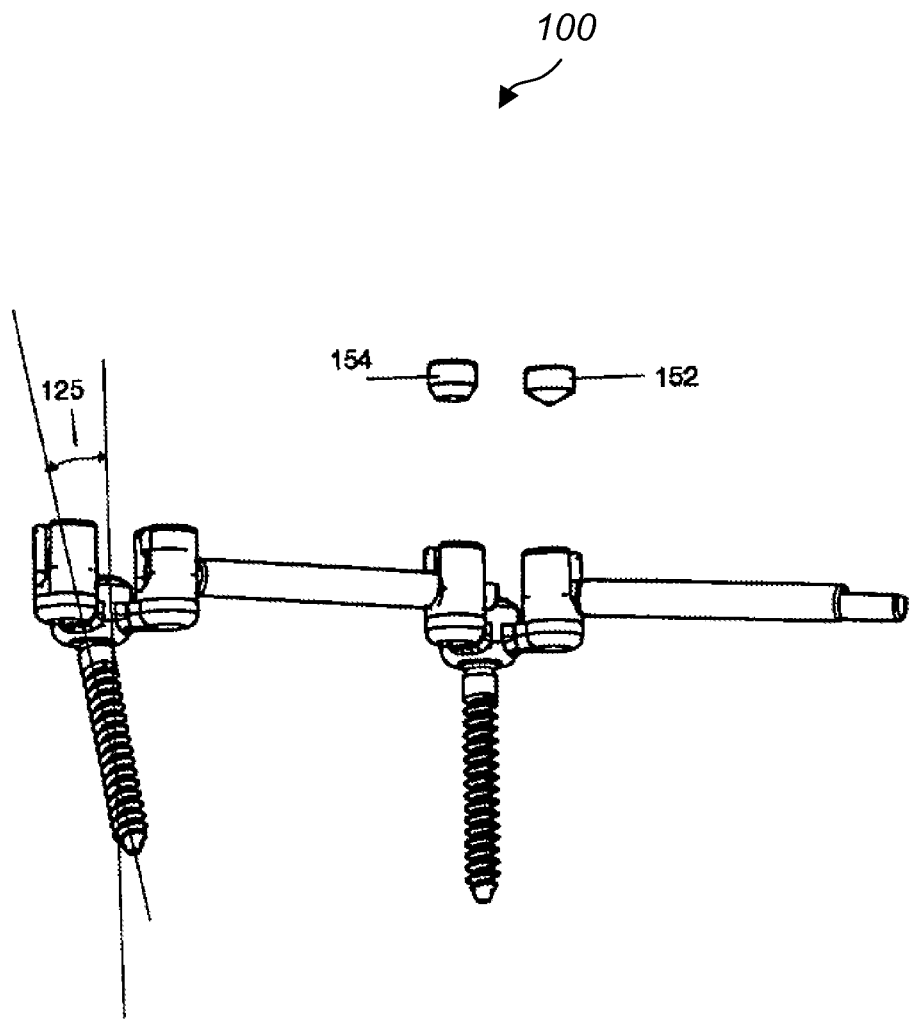
FIG. 3 is a side view of the spine fixation apparatus of FIG. 1.
Figure 4:
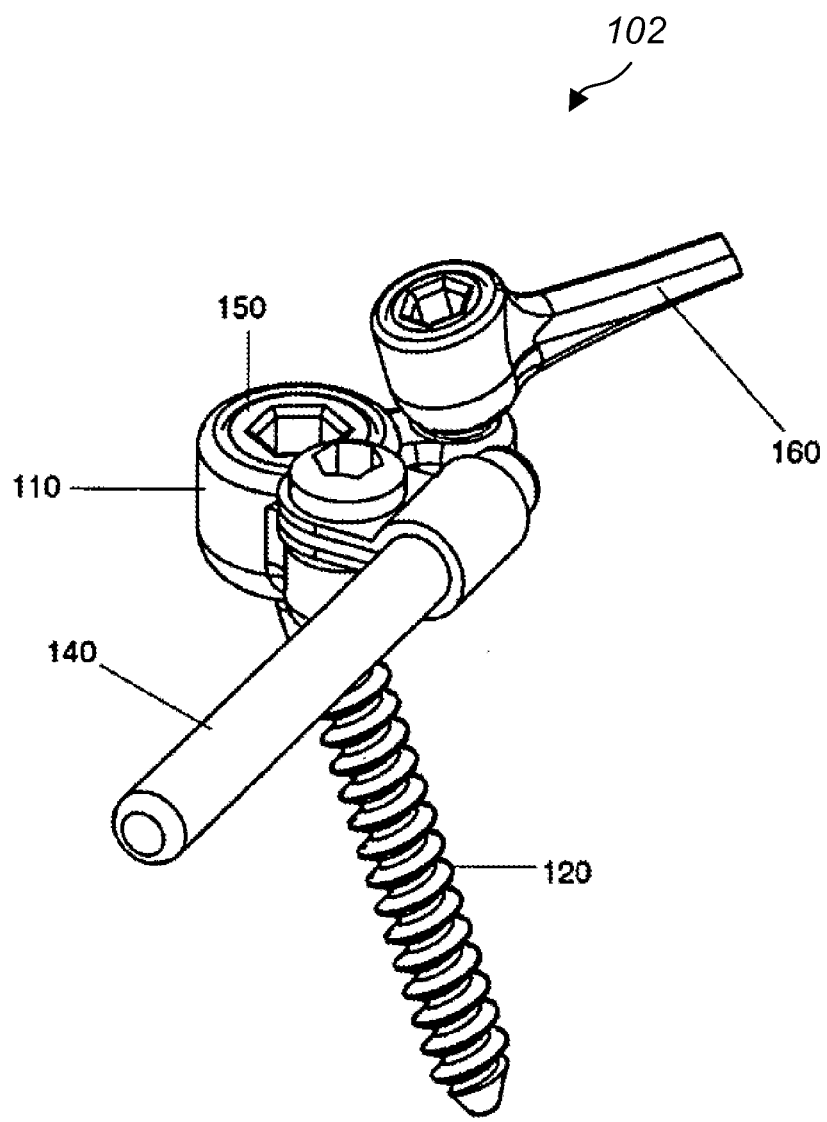
FIG. 4 is a perspective view of another embodiment of an improved spine fixation apparatus that utilizes a multi-axial screw assembly that accommodates both stabilization rods and plates.
Figure 5:
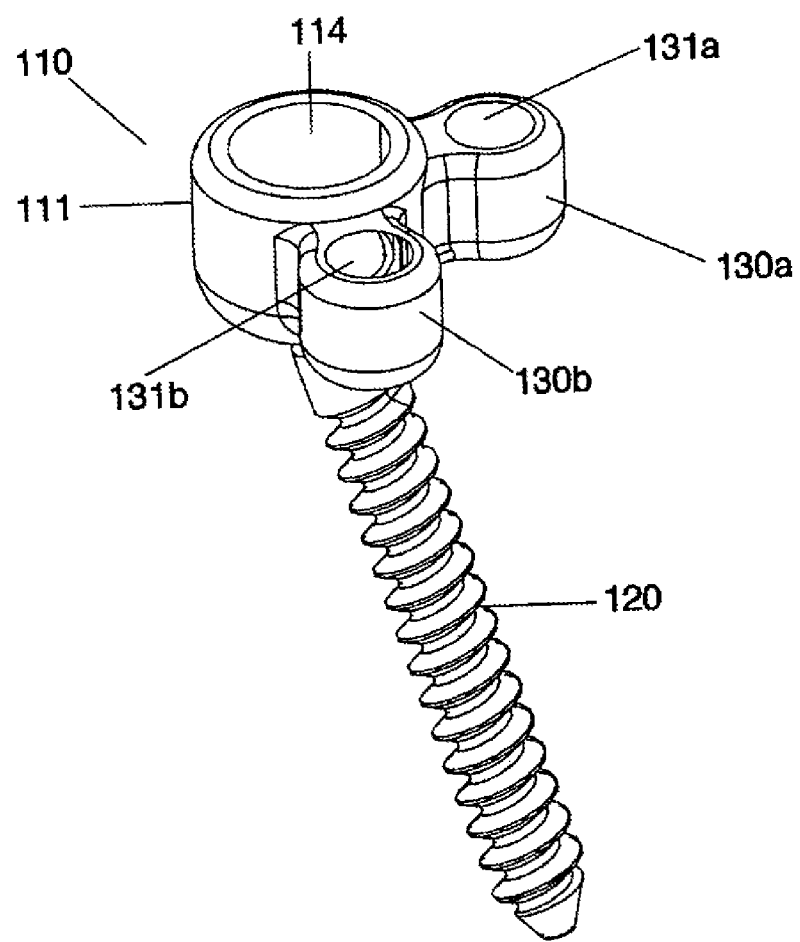
FIG. 5 is a perspective view of the multi-axial screw assembly of FIG. 4.
Figure 6:
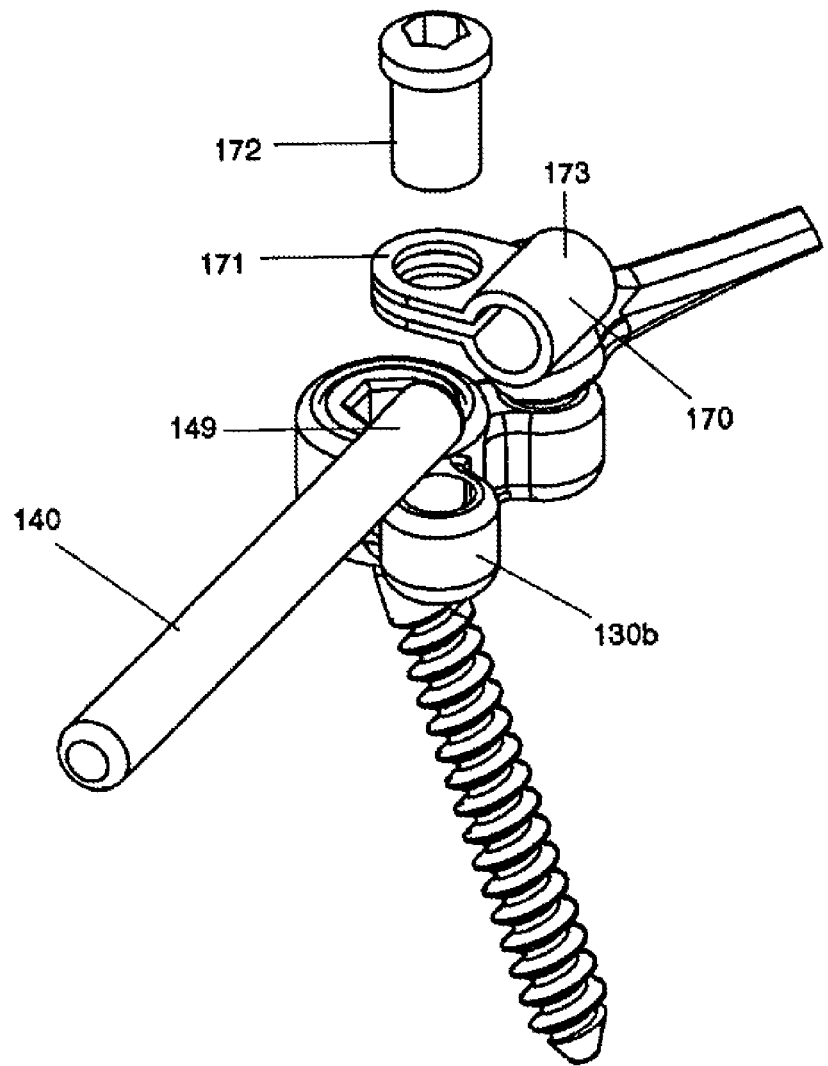
FIG. 6 is a partially exploded view of the spine fixation apparatus of FIG. 4.
Figure 7:
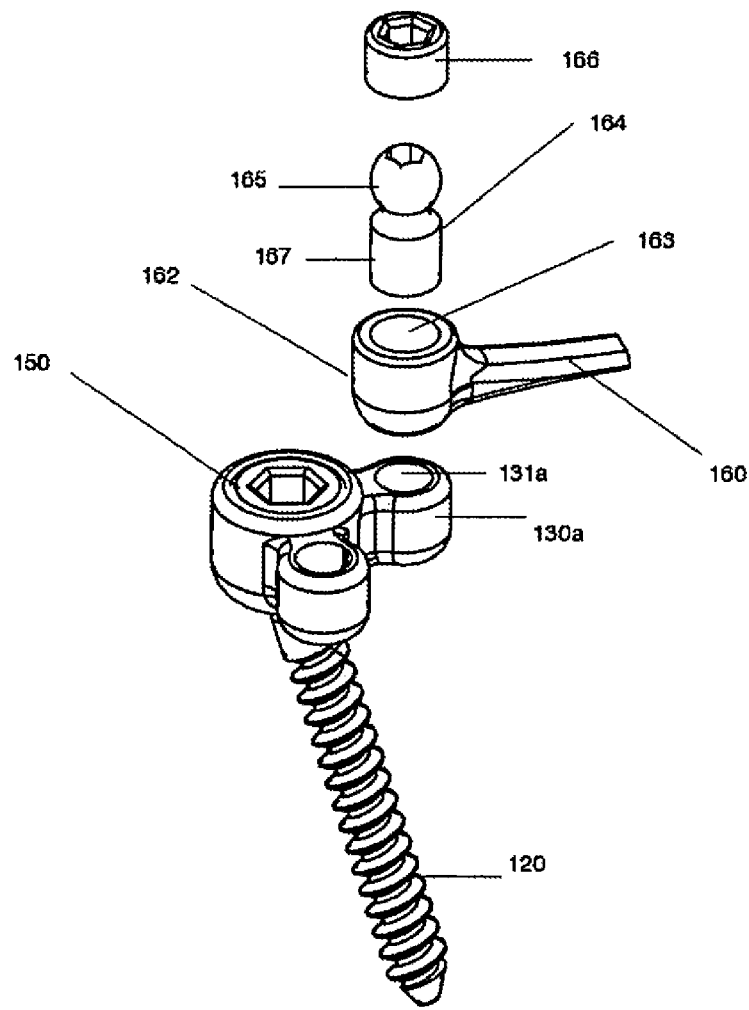
FIG. 7 is another partially exploded view of the spine fixation apparatus of FIG. 4.

Referring to FIG. 4, in another embodiment, a spine fixation assembly 102 includes a mounting assembly 110 a stabilization rod 140 attached to the mounting assembly 110 and a stabilization plate 160, also attached to the mounting assembly 110. Referring to FIG. 5, the mounting assembly 110 includes a screw housing 111 and two fixed mounting elements 130a, 113b extending from the housing 111. The screw housing 111 includes a through opening 114 for receiving a bone screw 120. Opening 114 extends from the top surface of the screw housing 111 to the bottom surface and has a diameter at the top larger than the diameter at the bottom. The bone screw 120 has a body 121 with outer threads and a spherical head 122. The body 121 is inserted through the opening 114 and is threaded into a vertebral bone (not shown). The spherical head 122 sits in the opening 114 of the screw housing 111 and the bone screw 120 is oriented at an angle 125 relative to the housing 111, as shown in FIG. 3. This orientation of the screw 120 relative to the screw housing 111 is secured by a setscrew 150. Set screw 150 has outer threads that cooperate with inner threads of the opening 114. In this embodiment the mounting elements 130a, 130b are fixed relative to the screw housing 111 and relative to each other. The mounting elements 130a, 130b have a cylindrical shape and threaded openings 131a, 131b, respectively. Referring to FIG. 6, end 149 of the stabilization rod 140 is inserted in a bracket 170 that has a cylindrically shaped body 173 for receiving the cylindrically shaped rod end 149, and a loop 171 extending from the side of the cylindrical body 173. The loop 171 is placed onto the mounting element 130b and is attached to it by inserting a set screw 172 through the loop 171 and screwing it into the opening 131b. Referring to FIG. 7, a cup shaped end 162 of the stabilization plate 160 is placed onto the mounting element 130a and is attached to it with a plate screw 164. Plate screw 164 has a spherical head 165 and a threaded cylindrical bottom 167. The plate screw 164 is inserted through the cup opening 163 and the cylindrical bottom is screwed into the threaded opening 131a. The spherical head 165 sits in the cup opening 163. The plate 160 is positioned at a desired angle relative to the screw housing 111 and the position is locked with a set screw 166 placed on top of the spherical head 165 and tightened down into the cup opening 163. The set screw surface that interfaces with the spherical heard 165 of the plate screw 164 is concave and concentric with the spherical head 165.

Figure 8:
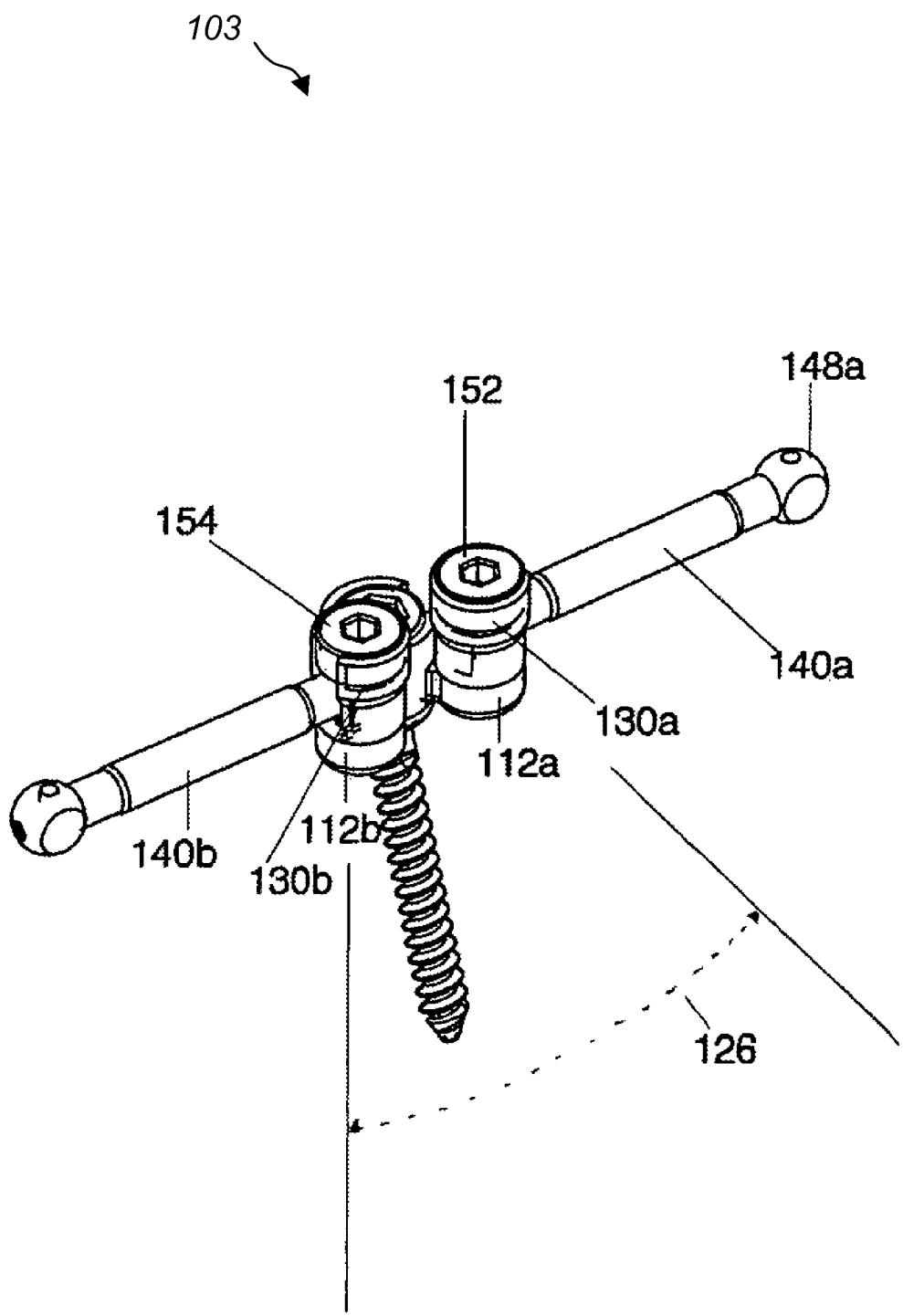
FIG. 8 is a perspective view of another embodiment of an improved spine fixation apparatus that utilizes a multi-axial screw assembly.
Figure 9:
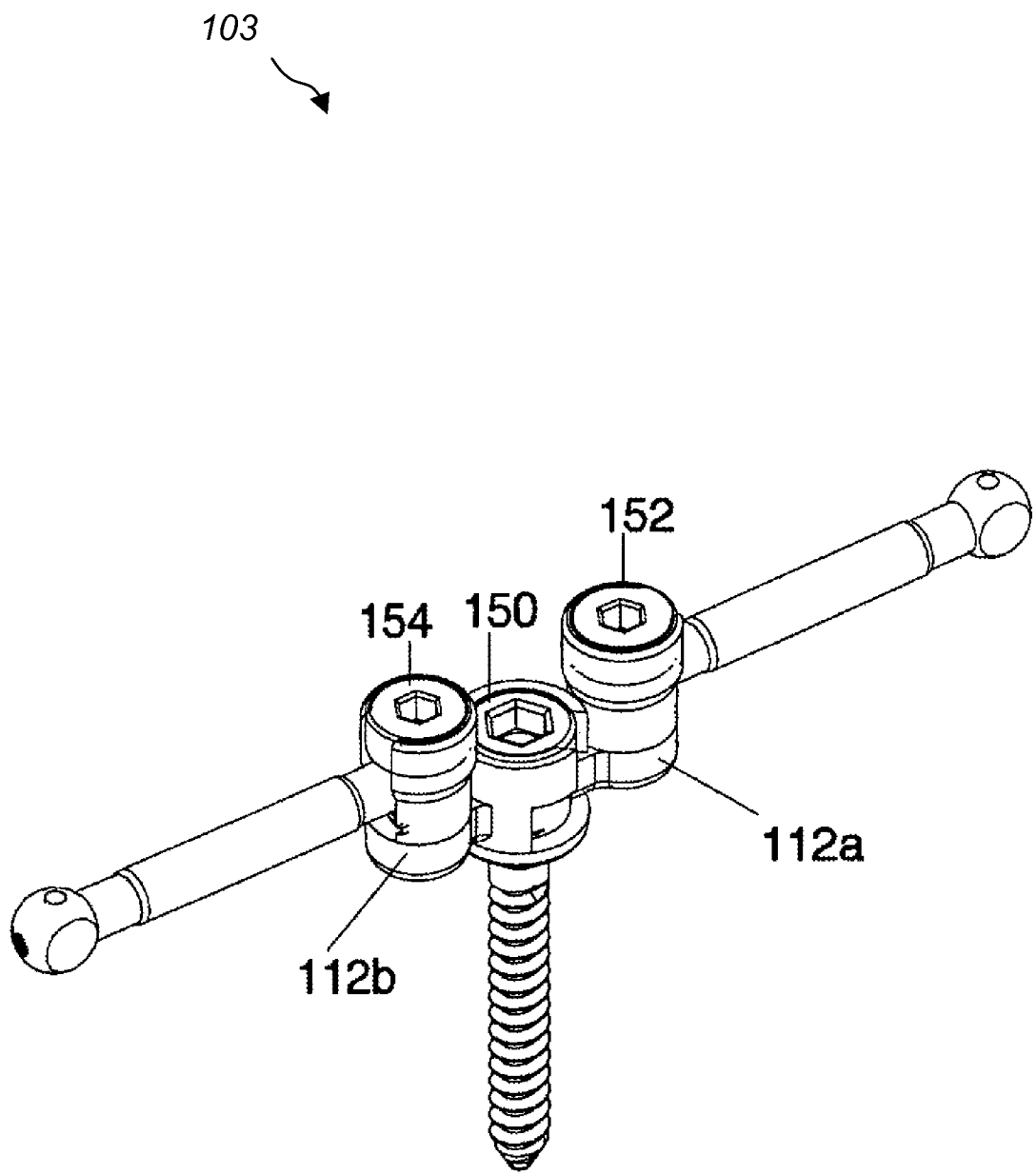
FIG. 9 is a perspective view of the multi-axial screw assembly of FIG. 8 with the mounting plates arranged at 180 degrees relative to each other.
Figure 10:
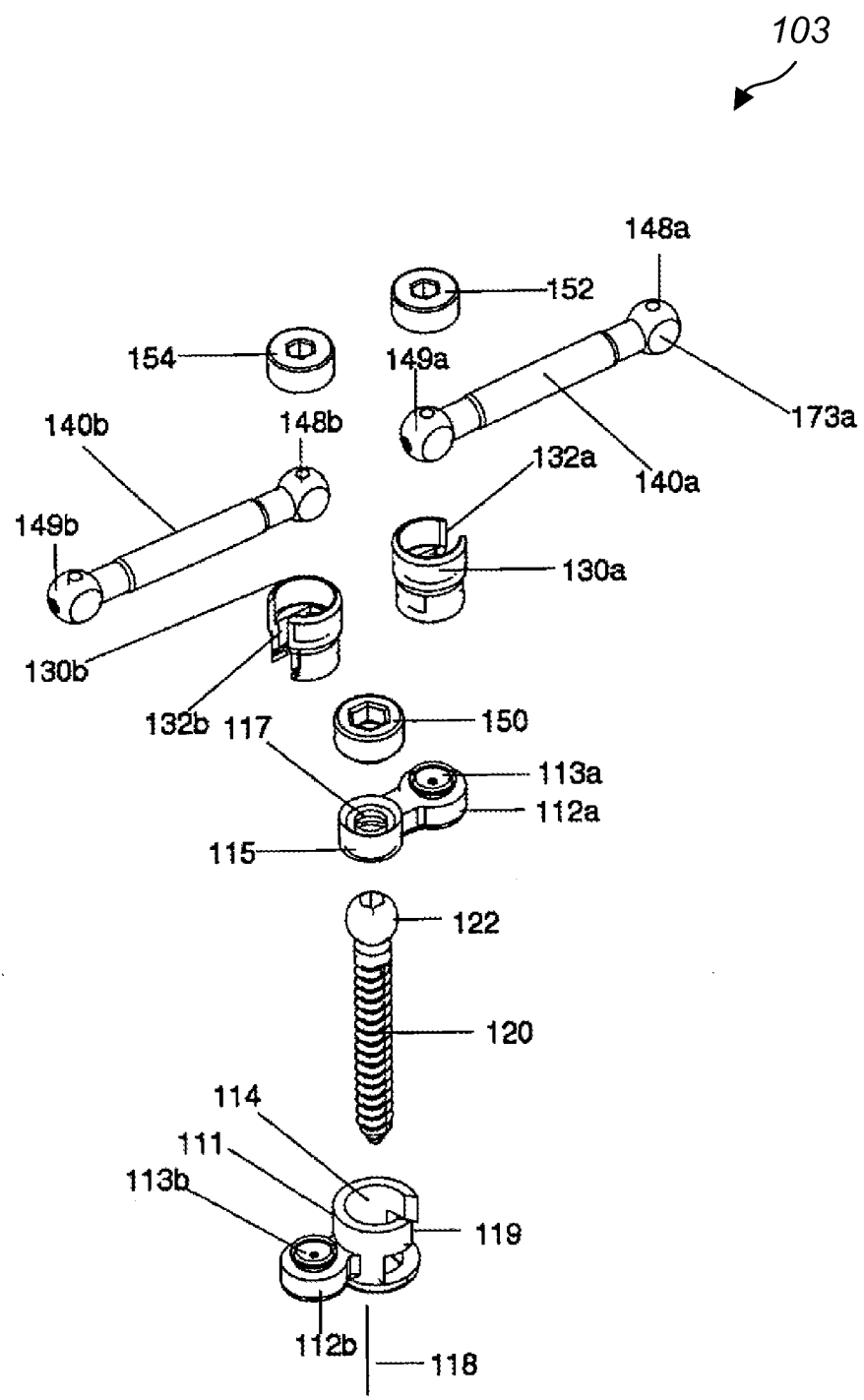
FIG. 10 is an exploded view of the spine fixation apparatus of FIG. 8.

Referring to FIG. 8, in another embodiment the spine fixation assembly 103 includes mounting assemblies 110a, 110b (not shown) and stabilization rods 140a, 140b. Stabilization rods 140a, 140b are placed and secured in the mounting assembly 110a. Referring to FIG. 10, the mounting assembly 110a includes a multiaxial screw housing 111, a fixed mounting plate 112b extending from the housing 111 and a movable mounting plate 112a. The movable mounting plate 112a has an end 115 that is inserted in a side opening 119 of the housing 111 and is allowed to swivel around axis 118 of the housing 111 thereby allowing the angle 126 between the mounting plates 112a, 112b to be adjusted. Axis 118 passes through the center of housing 111. In other embodiments axis 118 may pass through any other location of the mounting plate 112a. In the example of FIG. 8 the angle 126 is set to 90 degrees and in the example of FIG. 9, the angle 126 is set to 180 degrees. The screw housing 111 includes a through opening 114 for receiving a bone screw 120. Opening 114 extends from the top surface of the screw housing 111 to the bottom surface and has a diameter at the top larger than the diameter at the bottom. The end 115 of the movable mounting plate 112 that is inserted in the side opening 119 of the housing 111 also has a through opening 117 that is concentric with the opening 114. The bone screw 120 has a body 121 with outer threads and a spherical head 122. The body 121 is inserted through the openings 114 and 117 and is threaded into a vertebral bone (not shown). The spherical head 122 sits in the opening 114 of the screw housing 111 and the bone screw 120 is oriented at an angle 125 relative to the housing 111. This orientation of the screw 120 relative to the screw housing 111 is secured by a setscrew 150. Set screw 150 also secures the angle and positioning of the mounting plates 112a, 112b relative to each other and the housing 111. The mounting plates 112a, 112b have receiving elements 113a, 113b, that are used to attach the mounting elements 130a, 130b to the mounting plates 112a, 112b, respectively. The mounting elements 130a, 130b have a cylindrical shape and side slot openings 132a, 132b, respectively, shaped and dimensioned to accommodate the ends 149a, 148b of the stabilization rods 140a, 140b, respectively. Mounting elements 130a, 130b may also rotate around an axis passing through their center. Each stabilization rod 140a, 140b has an elongated cylindrical body, and spherical ends 148a, 149a, 148b, 149b, respectively. The spherical ends 148a, 149a, 148b, 149b, have flat sides 173a, 173b opposite to each other. The spherical end 149a of rod 140a is placed in the slot opening 132a of the mounting element 130a and the spherical end 148b of rod 140b is placed in the side slot opening 131b of the mounting element 130b and are secured with set screws 152, 154, respectively. The flat sides 177a, 177b are oriented parallel to walls of the side slot openings. Set screws 152, 154 secure the angular position of the rods 140a, 140b relative to the mounting elements 130a, 130b and therefore relative to the screw housing 111.

Figure 11:
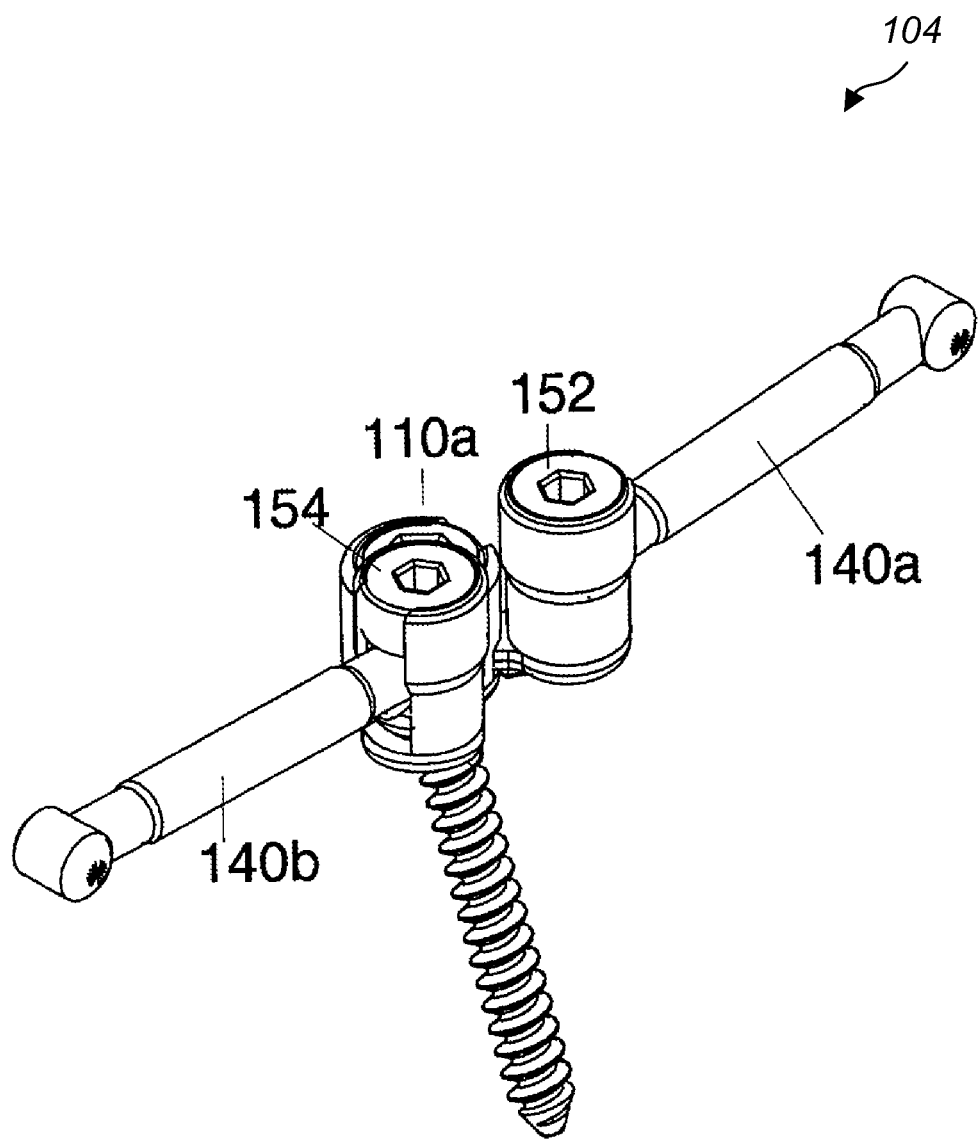
FIG. 11 is a perspective view of another embodiment of an improved spine fixation apparatus that utilizes a multi-axial screw assembly.
Figure 12:
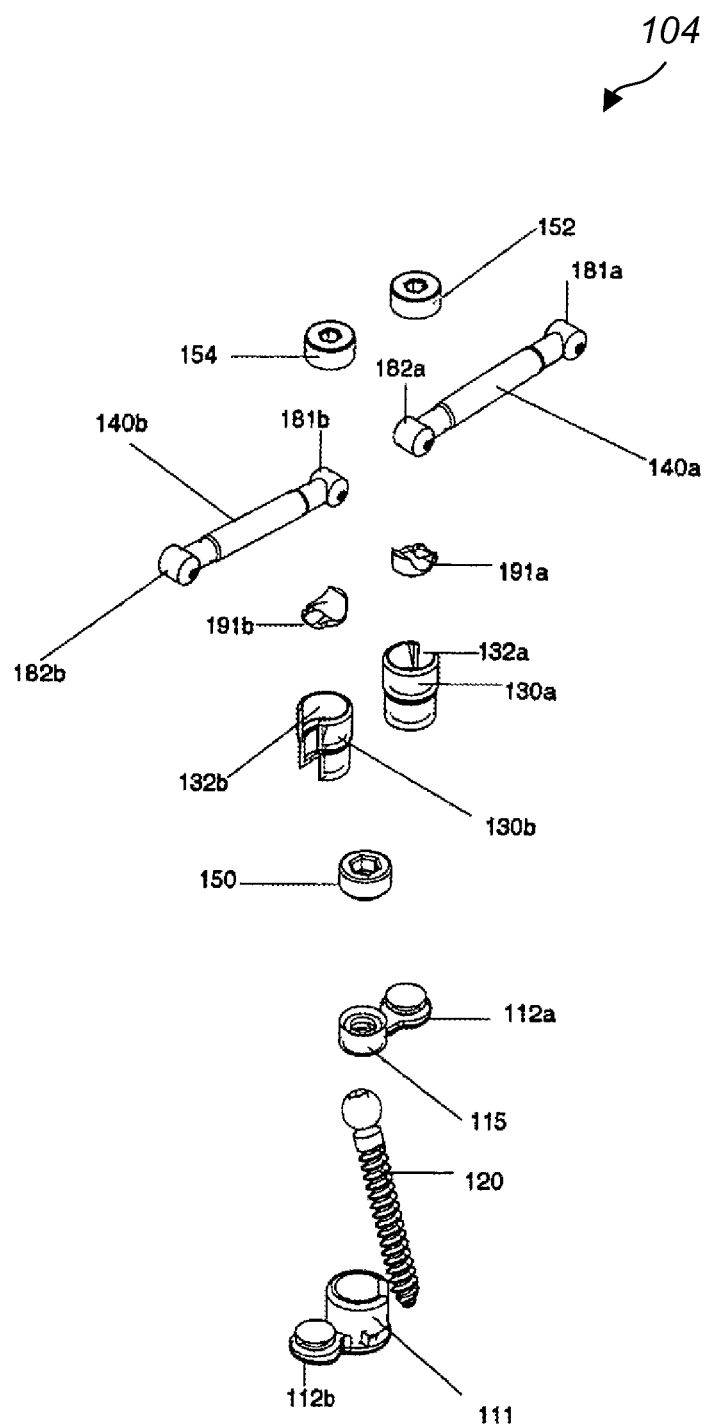
FIG. 12 is an exploded view of the spine fixation apparatus of FIG. 1.

Referring to FIG. 11, in another embodiment 104 of the spine fixation assembly the stabilization rods have hammer shaped rod ends 181a, 182a, 181b, 182b. The mounting elements 130a, 130b have a cylindrical shape, side slot openings 132a, 132b, respectively, and accommodate nesting seats 191a, 191b, respectively, shaped and dimensioned to accommodate the hammer shaped ends 182a, 181b of the stabilization rods 140a, 140b, respectively.

The screws 120 may be inserted in any location of adjacent vertebras or even in the same vertebra. Typical vertebral location for inserting screws include the pedicles, the vertebral body, the spinous process, the transverse processes the lamina, the sacrum, lateral mass, pars and the occiput.

In one example, spine fixation assembly 100 is made of titanium metal. In other examples the spine fixation assembly 100 is made of stainless steel, nickel, gold, silver or alloys thereof, composites, ceramics, plastic, bone, absorbable material or combination thereof. In one example, bone screw 120 has a length of 57 millimeters and a diameter of 6.5 millimeters. The stabilization rods may have a length in the range of 20 millimeters to 200 millimeters. Other embodiments include the following. A hook may be used instead for a bone screw. Rotation axis 118 may be perpendicular to plate 112a and pass through a location of plate 112a between the receiving element 113a and end 115. In this case, receiving element may connect to plate 112a via a hinge mechanism or any other connection mechanism that allows rotational motion. Spine fixation assembly 100 may be implanted via a minimally invasive surgical procedure or an open surgery procedure. Spine fixation assembly 100 my be assembled before surgical implantation or after surgical implantation of the components.

Several embodiments of the present invention have been described. Nevertheless, it will be understood that various modifications may be made without departing from the spirit and scope of the invention. Accordingly, other embodiments are within the scope of the following claims.

What is claimed is:

1. A spine fixation assembly connecting a first vertebra to a second vertebra comprising:
    a first mounting assembly configured to be attached to a first location of said first vertebra and comprising a first bone anchor housing and first and second spinal stabilization component housings extending from said first bone anchor housing,
    a second mounting assembly configured to be attached to a first location of said second vertebra and comprising a second bone anchor housing and third and fourth spinal stabilization component housings extending from said second housing,
    a first spinal stabilization component comprising an elongated body having a first end and a second end and being configured to connect said first mounting assembly to said second mounting assembly, and
    wherein said first spinal stabilization component housing is adapted to receive and connect to said first end of said spinal stabilization component and said third spinal stabilization component housing is adapted to receive and connect to said second end of said spinal stabilization component.

2. The spine fixation assembly of claim 1 wherein any of said spinal stabilization component housings comprise a mounting plate extending from said bone anchor housing and a mounting element configured to be removably attached to said mounting plate.

3. The spine fixation assembly of claim 2 wherein said mounting element is rotatable around an axis passing through its center.

4. The spine fixation assembly of claim 1 wherein each of said spinal stabilization component housings is rotatable around an axis passing through the center of said corresponding bone anchor housing.

5. The spine fixation assembly of claim 1 wherein any of said bone anchor housings comprise a multi-axial bone anchor housing.

6. The spine fixation assembly of claim 1 wherein said spinal stabilization component is selected from a group consisting of rods, plates, cables and wires.

7. The spine fixation assembly of claim 1 wherein said first and second ends of said elongated body comprise a geometric configuration selected from a group consisting of sphere, cylinder, hemisphere, flat plate, cup, hammer, sphere with flat opposite surfaces, circular plate, semicircular plate, polyhedron, ring-shaped and cannulated shape.

8. The spine fixation assembly of claim 1 further comprising a bone anchor and wherein any of said mounting assemblies is attached to said vertebral location via said bone anchor configured to be received within said bone anchor housing.

9. The spine fixation assembly of claim 8 wherein said bone anchor is selected from a group consisting of screws, hooks and pins.

10. The spine fixation assembly of claim 8 wherein said bone anchor comprises a poly-axial screw.

11. The spine fixation assembly of claim 1 wherein any of said mounting elements comprise a seat having a bottom configured to be removably attached to said corresponding mounting plate and a top configured to receive any of said elongated body's ends and comprising a side portion having an opening through which said elongated body extends.

12. The spine fixation assembly of claim 1 further comprising a first locking element for securing said first end to said first mounting element and a second locking member for securing said second end to said third mounting element.

13. The spine fixation assembly of claim 12 further comprising a bone anchor locking element for securing a bone anchor head to any of said bone anchor housings.

14. The spine fixation assembly of claim 13 wherein any of said locking elements comprise at least one of a screw, a screw with a flat bottom, a screw with a pointed bottom, a washer, a nut, a snap-in lock, or a breakaway screw.

15. The spine fixation assembly of claim 14 further comprising a third spinal stabilization component configured to connect said third mounting assembly to a fourth mounting assembly configured to be attached to a first location of a fourth vertebra.

16. The spine fixation assembly of claim 1 further comprising a second spinal stabilization component configured to connect said second mounting assembly to a third mounting assembly configured to be attached to a first location of a third vertebra.

17. The spine fixation assembly of claim 1 wherein said first and second vertebras are adjacent vertebras.

18. The spine fixation assembly of claim 1 wherein said first and second vertebras are not adjacent vertebras.

19. The spine fixation assembly of claim 1 wherein said locations of said vertebras are selected from a group consisting of a pedicle, transverse processes, pars, lamina, vertebral body, sacrum, lateral mass, and occiput.

20. The spine fixation assembly of claim 1 comprising a material selected from a group consisting of stainless steel, titanium, gold, silver, nickel, alloys thereof, bone, polymer, composites, ceramics, plastic, absorbable material and combination thereof.

21. The spine fixation assembly of claim 1 wherein said spinal stabilization component comprises adjustable length.

22. A mounting assembly configured to be attached to a vertebra comprising:
    a bone anchor;
    a bone anchor housing configured to receive said bone anchor for attaching said assembly to said vertebra;
    first and second spinal stabilization component housings extending from said bone anchor housing, wherein each of said first and second spinal stabilization components is adapted to receive an end of a first or second spinal stabilization components, respectively, and thereby to connect said mounting assembly to other mounting assemblies configured to be attached to other vertebras;
    wherein each of said spinal stabilization component housings comprises a mounting plate extending from said bone anchor housing and a mounting element configured to be removably attached to said mounting plate; and
    wherein each of said mounting elements comprises a seat having a bottom configured to be removably attached to a corresponding mounting plate and a top configured to receive an end of either of said first and second spinal stabilization component, respectively and wherein each of said mounting elements further comprises a side portion having an opening shaped so that one of said first and second spina stabilization components extends through said opening.

23. The mounting assembly of claim 22 wherein said bone anchor comprises a poly-axial screw.

24. The mounting assembly of claim 22 wherein each of said mounting elements is rotatable around an axis passing through a center of a respective mounting plate.

25. The mounting assembly of claim 22 further comprising locking elements for securing said bone anchor to said bone anchor housing and said spinal stabilization components to said mounting elements, respectively.

26. A spine fixation method connecting a first vertebra to a second vertebra comprising:
providing a first mounting assembly comprising a first bone anchor housing and first and second spinal stabilization component housings extending from said first bone anchor housing,
attaching said first mounting assembly to a first location of said first vertebra,
providing a second mounting assembly comprising a second bone anchor housing and third and fourth spinal stabilization component housings extending from said second housing,
attaching said second mounting assembly to a first location of said second vertebra
providing a first spinal stabilization component comprising an elongated body having a first end and a second end and being dimensioned to span the distance between said first mounting assembly and said second mounting assembly,
attaching said first end of said spinal stabilization component to said first spinal stabilization component housing, and
attaching said second end of said spinal stabilization component to said third spinal stabilization component housing.

27. The spine fixation method of claim 26 wherein any of said spinal stabilization component housings comprise a mounting plate extending from said bone anchor housing and a mounting element configured to be removably attached to said mounting plate.

28. The spine fixation method of claim 26 wherein each of said spinal stabilization component housings is rotatable around an axis passing through the center of said corresponding bone anchor housing.

29. The spine fixation method of claim 26 wherein any of said bone anchor housings comprise a multi-axial bone anchor housing.

30. The spine fixation method of claim 26 wherein said spinal stabilization component is selected from a group consisting of rods, plates, cables and wires.

31. The spine fixation method of claim 26 wherein said first and second ends of said elongated body comprise a geometric configuration selected from a group consisting of sphere, cylinder, hemisphere, flat plate, cup, hammer, sphere with flat opposite surfaces, circular plate, semicircular plate, polyhedron, ring-shaped and cannulated shape.

32. The spine fixation method of claim 26 wherein any of said mounting assemblies is attached to said vertebral location via a bone anchor configured to be received within said bone anchor housing.

33. The spine fixation method of claim 32 wherein said bone anchor is selected from a group consisting of screws, hooks and pins.

34. The spine fixation method of claim 32 wherein said bone anchor comprises a poly-axial screw.

35. The spine fixation method of claim 26 wherein any of said mounting elements comprise a seat having a bottom configured to be removably attached to said corresponding mounting plate and a top configured to receive any of said elongated body's ends and comprising a side portion having an opening through which said elongated body extends.

36. The spine fixation method of claim 26 further comprising securing said first end to said first spinal stabilization component housing with a first locking element and securing said second end to said third spinal stabilization component housing with a second locking element.

37. The spine fixation method of claim 36 further comprising securing a bone anchor head to any of said bone anchor housings with a bone anchor locking element.

38. The spine fixation method of claim 37 wherein any of said locking elements comprise at least one of a screw, a screw with a flat bottom, a screw with a pointed bottom, a washer, a nut, a snap-in lock, or a breakaway screw.

39. The spine fixation method of claim 26 further comprising providing a second spinal stabilization component and connecting a first end of said second stabilization component to said second mounting assembly and a second end of said spinal stabilization component to a third mounting assembly configured to be attached to a first location of a third vertebra.

40. The spine fixation method of claim 39 further comprising providing a third spinal stabilization component and attaching a first end of said third spinal stabilization component to said third mounting assembly and a second end of said third spinal stabilization component to a fourth mounting assembly configured to be attached to a first location of a fourth vertebra.

41. The spine fixation method of claim 26 wherein said locations of said vertebras are selected from a group consisting of a pedicle, transverse processes, pars, lamina, vertebral body, sacrum, lateral mass, and occiput.

* * * * *